United States Patent [19]

Carruth et al.

[11] Patent Number: Plant 6,910

[45] Date of Patent: Jul. 11, 1989

[54] HYBRID TEA ROSE PLANT CV. AROREROY

[75] Inventors: Thomas F. Carruth, Canoga Park; Jack E. Christensen, Ontario, both of Calif.

[73] Assignee: Bear Creek Gardens, Inc., Medford, Oreg.

[21] Appl. No.: 67,560

[22] Filed: Jun. 26, 1987

[51] Int. Cl.[4] ..... A01H 5/00

[52] U.S. Cl. ..... Plt./21

[58] Field of Search ..... Plt./21

*Primary Examiner*—Robert E. Bagwill

*Attorney, Agent, or Firm*—Majestic, Parsons, Siebert & Hsue

[57] ABSTRACT

A new hybrid tea rose for cut flowers, having as its seed parent Red Success, and as its pollen parent, Royalty (U.S. Plant Pat. No. 4,057). The plant is a tall greenhouse seedling of the bush type, producing an abundance of large, strongly tea-scented blossoms that are deep red in color. The flowers' long, strong stems and urn-shaped buds make them very suitable for cutting. The plants bloom continually in the greenhouse throughout the year. Blossoms on long stems cut from plants of the new variety grown in a greenhouse last at living room temperatures for 6 to 7 days.

1 Drawing Sheet

This invention relates to a new variety of hybrid tea rose cv. Aroreroy. The plant is a tall, greenhouse seedling of the bush type, cultivated for cut flowers. Its hardiness is yet untested. It was bred by Thomas E. Carruth and Jack E. Christensen in Ontario, Calif., and has as its seed parent, Red Success and as its pollen parent, Royalty (U.S. Plant Pat. No. 4,057).

The new variety cv. Aroreroy may be distinguished from other presently available commercial rose cultivars by the following combination of characteristics: its large urn-shaped buds of an even toned red color, borne on long, strong stems, which make its strongly tea-scented flowers very suitable for cutting essentially as described and illustrated herein. Aroreroy holds these distinguishing characteristics through succeeding propagations by cutting, budding, and tissue culture.

The new rose may be distinguished from its seed parent, Red Success, by the following combination of characteristics: Whereas the seed parent bears flowers of a orange-red coloration, Aroreroy bears flowers of a truer red coloration, essentially as described and illustrated herein. The new variety bears flowers having fewer petals than flowers of Red Success. Buds of Aroreroy are more pointed in form than buds of the seed parent. Plants of Aroreroy are more productive than plants of Red Success.

The new variety may be distinguished from its pollen parent, Royalty (U.S. Plant Pat. No. 4,057) by the following combination of characteristics: Whereas Royalty produces flowers of a deep red coloration, the new variety produces flowers of a lighter red coloration essentially as described and illustrated herein. The stems of Royalty have a tendency to develop slight "crooks" whereas the stems of Aroreroy grow very straight and erect.

The accompanying drawing illustrates the plant in color and shows the flowering thereof from bud to full bloom. Throughout this specification, color names beginning with a small letter signify that the name of that color as used in common speech is aptly descriptive. Color names beginning with a capital letter designate values based upon the R.H.S. Colour Chart of The Royal Horticultural Society of London, England.

The descriptive matter which follows pertains to roses of the new variety grown in a greenhouse in southern California and is believed to apply to plants of the variety grown in similar conditions of soil and climate elsewhere.

FLOWER

The new variety almost always bears its flowers singly, sometimes two to three flowers per stem. Flowers are borne on strong stems that are long for the class. In the greenhouse, the plant blooms freely and continuously year round. Flowers have a strong tea fragrance.

BUD

The peduncle is of average length to long for the class, of average to heavy caliper, and erect. It is moderately smooth, with some stipitate glands, and few small prickles. Bud color is near Yellow-Green 144A.

Before the calyx breaks, the bud is of medium size for the class, medium in length, and pointed and ovoid in form. The surface of the bud bears a few foliaceous appendages, tomentum and stipitate glands. Deeply serrate foliaceous parts are usually present, extending beyond the tip of the bud and equal to three quarters or more of its length.

As the calyx breaks, bud color is near Red-Purple 59A.

The inner surface of the sepals has a fine tomentum; margins are lined with stipitate glands and hairs.

As the first petal opens, the bud is large in size for the class, long and pointed to urn-shaped in form. The outside and inside surface of the newly-opening petals is Red-Purple 59A in color. The bud opens up well and is not prevented from opening by hot, wet, or dry weather. Production of large-sized buds is maintained during the summer heat.

BLOOM

When fully open, the bloom is large for the class, ranging from $3\frac{1}{2}$ to $4\frac{1}{2}$ inches in diameter. Petalage is double, with petals arranged regularly; there are from 28 to 32 petals present and from 2 to 4 petaloids. When half open, the bloom is flat topped, and the petals are spiraled with petal edges somewhat reflexed to rolled outward. When fully open, the bloom is somewhat cupped, with petals loosely cupped and petal edges slightly undulated.

The petals are of moderately heavy substance and of medium thickness, with insides slightly satiny and outsides slightly velvety. The outside petals are nearly round in shape, sometimes scalloped, with rounded apices, sometimes with one notch. The intermediate petals are round to broadly obovate in shape, with rounded apices, sometimes with one notch. The inner petals are nearly oval, sometimes scalloped, with rounded apices, sometimes with one notch.

The paragraphs immediately following describe the color values observed in a newly opened flower on a plant grown in a greenhouse in Somis, Calif., in the month of May.

The outside and inside surface of the outside petals is near Red 53A in color.

The outside and inside surface of the intermediate petals is near Greyed-Purple 187C in color.

The outside and inside surface of the inner petals is near Greyed-Purple 187B in color.

The paragraphs immediately following describe the color values observed in a bloom which had been open for three days indoors.

The outside and inside surface of the outside petals is between Red 53A and Red 46A in color.

The outside and inside surface of the inside petal is near Red 53B in color.

The general color effect of the newly opened flower is that of an even toned red, very bright with no near-black pigmentation. The petals usually drop off cleanly and are not particularly affected by hot or dry weather.

In May, blossoms on long stems cut from plants of the new variety grown in a greenhouse last at living room temperatures from 6 to 7 days.

REPRODUCTIVE ORGANS

Stamens are few to average in number and are arranged regularly about the pistils; a few are mixed with petaloids. The filaments are of medium length, and a few are without anthers. The anthers are of medium to large size, and all open at approximately the same time. Anther color is near Yellow 11B when immature and near Yellow 11A at maturity. Pollen is present in moderate amounts. Pollen color is near Yellow 11A.

The styles are uneven, of average length, of average caliper, and somewhat bunched. The stigma is near Yellow 8C in color. Ovaries are usually enclosed in the calyx, although some may protrude from the calyx.

Hips are of average length, oblong in form, and varying between Orange-Red 31A and Greyed-Green 194A in color. The sepals are permanent; sepals are short. The inside surface of the sepals is Yellow-Green 144C in color. The outside surface of the sepals is Yellow-Green 147B in color. Seeds are average in number (10 to 16).

FOLIAGE

The compound leaves are borne in normal quantities and usually comprise from three to five to seven leaflets. The leaves are large in size for the class, somewhat leathery, and semi-glossy. The leaflets are oval in shape, with acute apices and acute bases; their margins are serrate.

The upper surface of the mature foliage is near Green 139A in color; its under surface is near Green 138C. The upper surface of the young foliage is near Green 136_, tinged with Greyed-Purple 185A. The under surface of the young foliage is near Green 138C tinged with Greyed-Purple 185C.

The rachis is heavy, grooved on its upper side, with some stipitate glands on its edges. The under side of the rachis is usually smooth with few prickles.

Stipules are of medium length, and have medium-length points turning out at an angle of usually more than 45°, slightly recurved toward the stem.

The plant displays an average resistance to mildew and blackspot as compared to other commercial varieties grown under comparable conditions in Somis, Calif.

GROWTH

The plant is of tall, upright, and branched habit. It displays very vigorous growth. The canes are of heavy caliper for the class.

The main stems are near Yellow-Green 146C. They bear several large prickles which are of medium length to long for the class. The large prickles are almost straight and have narrow bases of medium length; prickle color is near Greyed-Orange 165B. The main stems bear few small prickles, also near Greyed-Orange 165B in color.

The branches are of a color near Yellow-Green 148A, tinged with Red-Purple 60A. They bear several large prickles which are of medium length for the class and which are almost straight to hooked slightly downward, with bases of medium length. The large prickles are near Greyed-Purple 179C in color, and near Green 138D at the tip. The branches have no small prickles and no hairs.

New shoots are near Greyed-Green 191C in color overlayed with a near Greyed-Purple 185B. They bear several large prickles of medium length for the class which are hooked slightly downward, with narrow bases of medium length. Prickle color is near Greyed-Red 179C at the base, near Green 138D at the tip. There are no small prickles and no hairs.

I claim:

1. A new and distinct variety of hybrid tea rose plant cv. Aroreroy, the parts and asexual reproduction thereof, the plant being particularly characterized by its large urn-shaped buds of an even-toned red color, borne on long, strong stems, which make its strongly tea scented flowers very suitable for cutting, essentially as described and illustrated herein.

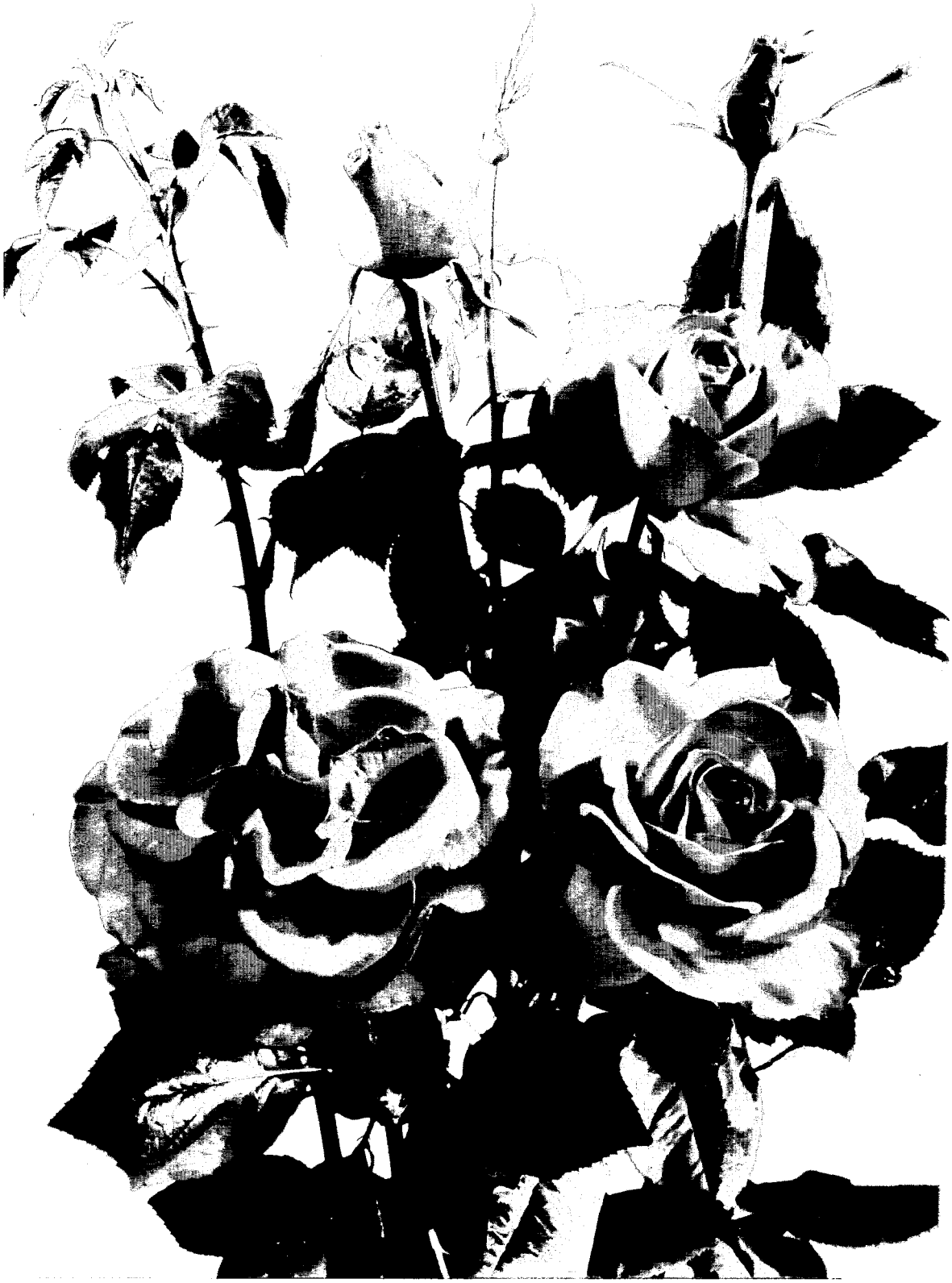

* * * * *